United States Patent

Graf et al.

[11] Patent Number: 5,864,994
[45] Date of Patent: Feb. 2, 1999

[54] GLAZING ELEMENT, IN PARTICULAR FOR FACING BUILDING FACADES

[75] Inventors: Wolfgang Graf, Eschbach; Andreas Georg; Volker Wittwer, both of Freiburg; Michael Koehl, Muellheim; Franz Brucker; Andreas Gombert, both of Freiburg; Ludwig Thomas, Berlin, all of Germany

[73] Assignee: Fraunhofer Gesellschaft zur Foerderung der angewandten Forschung e.V., Munich, Germany

[21] Appl. No.: 836,569

[22] PCT Filed: Nov. 14, 1995

[86] PCT No.: PCT/DE95/01573

§ 371 Date: Aug. 25, 1997

§ 102(e) Date: Aug. 25, 1997

[87] PCT Pub. No.: WO96/15348

PCT Pub. Date: May 23, 1996

[30] Foreign Application Priority Data

Nov. 14, 1994 [DE] Germany ............... 44 40 572.3

[51] Int. Cl.⁶ .................................................. E06B 7/00
[52] U.S. Cl. .................. 52/171.3; 359/360; 359/585; 359/589; 359/581; 359/275
[58] Field of Search ............... 52/171.3; 359/360, 359/581, 585, 589, 275

[56] References Cited

U.S. PATENT DOCUMENTS

| | | | |
|---|---|---|---|
| 3,718,528 | 2/1973 | Bergstrom | 161/1 |
| 4,017,265 | 4/1977 | Taylor | 428/675 |
| 4,338,000 | 7/1982 | Kamimori et al. | |
| 5,042,923 | 8/1991 | Wolf et al. | 52/171.3 X |
| 5,099,621 | 3/1992 | Schacklette et al. | 52/171.3 |
| 5,136,419 | 8/1992 | Shabrang | 359/275 X |
| 5,197,242 | 3/1993 | Baughman et al. | 52/171.3 |
| 5,503,884 | 4/1996 | Meyer et al. | 52/171.3 X |
| 5,666,771 | 9/1997 | Macquart et al. | 52/171.3 |

FOREIGN PATENT DOCUMENTS

| | | |
|---|---|---|
| 894 645 | 1/1983 | Belgium . |
| 1 596 819 | 4/1971 | Germany . |
| 24 36 174 | 2/1975 | Germany . |
| 58-000752 | 1/1983 | Japan . |
| 375 848 | 4/1964 | Switzerland . |

*Primary Examiner*—Christopher Kent
*Assistant Examiner*—Yvonne Horton-Richardson
*Attorney, Agent, or Firm*—Evenson, McKeown, Edwards & Lenahan, P.L.L.C.

[57] ABSTRACT

A glazing element, in particular, for facing building facades, having two panes enclosing a gaseous atmospheric intermediate space and having a predetermined layer on at least one pane surface facing the intermediate space. The glazing element is distinguished by the fact that the predetermined layer has a reactive layer applied on one pane and a catalytic layer applied on the reactive layer. The catalytic layer, depending on the composition of the gas atmosphere contained between the panes, activates in the reactive layer. The reaction changes the optical and/or electrical properties of the reactive layer, and varies the composition of the gas atmosphere in the intermediate space, thereby making the electrical and/or optical properties of the reactive layer variable.

27 Claims, 1 Drawing Sheet

GLAZING ELEMENT, IN PARTICULAR FOR FACING BUILDING FACADES

TECHNICAL FIELD

The present invention relates to a glazing element having at least two panes, in particular, for facing the facades of buildings.

STATE OF THE ART

A critical problem in using solar energy in buildings is controlling the flow of radiation through the windows and the glass facades. Frequently, the energy and light needs inside the building do not correlate to the solar energy input, leading either to overheating on sunny days or, if employing sun protection glass, to too low exploitation of the solar energy during the heating period. Although mechanical shading systems permit variable solar transmission, they often require intensive maintenance and therefore are expensive.

Presently, major efforts are being made to be able to control respectively to be able to switch the light transmitted through windows by means of so-called electrochrome layer systems, in which transmission is altered by adding ions. Usually these multi-layer systems comprise five layers: two conductive, transparent electrodes, one ion-conducting layer, one ion-storing layer and the active layer, e.g. wolfram oxide. Layer systems of this type are expensive to construct and the homogeneity of their switching behavior and their dependency on temperature are sources of problems.

The aforedescribed multi-layer systems are described in detail in U.S. Pat. No. 4,338,000 or DE-24 36 174 A1. These printed publications indicate, in particular, that the chromatic change is due to application of an external electric field. It large-surface glazing elements are employed for facing the facades of buildings, the electric energy required for the chromatic change would be quite large and therefore financially unattractive.

Furthermore, glazing elements of the aforedescribed type are not suited for rooms in which there is any danger of explosion, because large-surface electrodes, like those needed for applying voltage, presently involve a considerable risk of sparking.

Moreover, known are photochromic and thermochromic films on glazing elements which change their transmittance depending on light incidence or temperature. A drawback of these known films, however, is that transmission of photochromic films respectively thermochromic films cannot be arbitrarily switched. In this connection, reference is made to DE-A-1 596 B19 describing a process and glazing for uniforming the energy passing through the glazing in order to grant the glazing a variable transmissiveness is described.

SUMMARY OF THE INVENTION

The object of the present invention is to further improve a glazing element having at least two panes, in particular, for facing building facades in such a manner that, in order to make the glazing elements chromatically turbid, the energy requirements are not high and consequently that the degree of transmission can be individually adapted to the current radiation conditions. In particular, it should be possible to obviate the input of electric power.

DESCRIPTION OF THE INVENTION

The invented glazing element, in particular, for facing building facades, having two panes enclosing an intermediate space and having a layer structure provided on at least one of the pane surfaces facing the intermediate space as well as a gas atmosphere within the intermediate spate, distinguished by the fact that the layer structure has a reactive layer which is applied onto the surface of the one pane and a catalytic layer which is applied onto the reactive layer and which activates in the reactive layer a reaction which changes the optical and/or electrical properties of the reactive layer dependent on the composition of the gas atmosphere contained between the panes and by means for varying the composition of the gas atmosphere in the intermediate space being provided, thereby making the electrical and/or optical properties of the reactive layer variable.

The optical property, which can be reversibly altered by the reaction in the reactive layer, can, in particular, be the transmission of the layer structure respectively the energy transmission ratio for light in a specific spectral range.

According to certain preferred embodiments various materials, notably wolfram oxide, molybdenum oxide, titanium oxide, vanadium oxide, chromium oxide respectively ceric oxide are used for the reactive layer.

All the materials alter their transmission according to the respective reactions, with the various materials differing in color when "darkening". Moreover, they change their electric properties. For instance, in the case of wolfram oxide conductivity increases as a result of the reaction.

According to certain preferred embodiments, the thickness of the reactive layer, can be set to achieve, the desired maximum switching hub of the layer structure.

For instance, in the case of a layer thickness of 200 nm of wolfram oxide, transmission is 70% in an undarkened state and 30% in a darkened state. In the case of a layer thickness of 500 nm, the transmission is correspondingly 65% in an undarkened state and 3% in the darkened state.

Preferred as catalytic layers are platinum, rhodium, palladium and/or nickel layers with a thickness usually between 1 nm and 5 nm. The speed of the switching procedure and the transmission in the lightened state can be set by the thickness of the catalytic layer. For instance if the catalytic layer is 1 nm, the switching period of the film is less than approximately 1 second and if the thickness is 5 nm usually 30 seconds.

The reaction, by means of which the optical and/or electrical properties of the reactive layer are reversibly altered, can usually be triggered by changing the proportion of hydrogen and of oxygen of the gas atmosphere which is in contact with the layer structure. For coloring in an oxygenfree atmosphere, a hydrogen proportion of approximately 1% suffices. In order to reverse the coloring, the oxygen proportion of a hydrogenfree gas atmosphere only has to be raised by 0.5%. The percentages relate to an overall pressure of the gas atmosphere of approximately 1 bar. Furthermore, decoloring can occur by means of atmospheric air.

If switching of the transmission is desired only in the visible range of the spectrum of light, the invented layer structure can be combined with a low-$\epsilon$ layer, which reflects in the infrared range and is transmissive in the visible range. The low-$\epsilon$ layer can, by way of illustration, be a thin silver or semiconductor layer, such as indium tin oxide, The low-$\epsilon$ layer reduces, in particular, the thermal losses through the glazing element. The low-$\epsilon$ layer is preferably applied onto one of the inside surfaces of the opposite panes. In this manner, the thermal flow through the entire glazing element is interrupted. The invented layer structure can be applied to any substrate, such as glass and/or polymer substrates and/or metallic substrates.

BRIEF DESCRIPTION OF THE DRAWINGS

To make the invented glazing element more apparent, an advantageous embodiment thereof is illustrated in the figures.

DETAILED DESCRIPTION OF THE DRAWINGS

Figure 1:
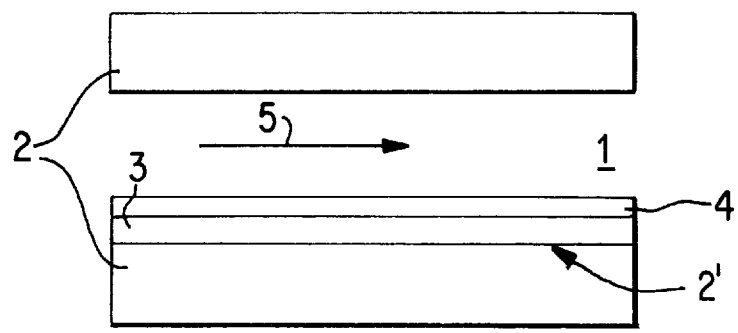
FIG. 1 shows a cross section of an advantageous embodiment of an invented glazing element

FIG. 1 shows a cross section of the invented glazing element. A layer structure having a reactive layer 3 and a catalytic layer 4, which is applied onto the reactive layer, is provided on the pane surface 2' of one of the two panes 2 enclosing the intermediate space 1. The layers can be produced by vapor deposition as well as by reactive sputtering.

The protons required for coloring the reactive layer 3, which preferably is composed of a wolfram oxide layer, are taken directly from the gas flow 5, which is conducted between the panes 2 in parallel, through the catalytic layer 4. In the absence of oxygen, a hydrogen part in the per mill range already suffices for coloring. For homogeneous coloring of the total area of the glazing element, the hydrogen concentration is tuned to the catalytic layer. On the other hand, input of an oxygen-containing gas, for instance air, suffices for decoloring.

Both these processes are reversible.

The use of electric current is completely obviated with the aid of the invented glazing element. This advantage reduces the layer structure of the glazing element considerably.

Figure 2:
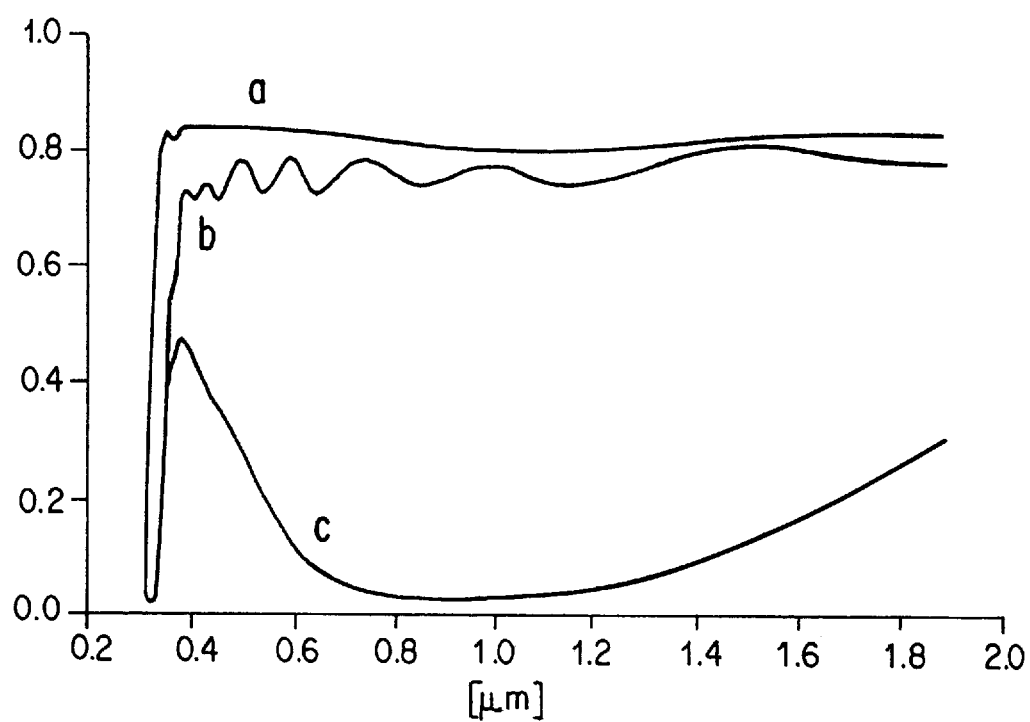
FIG. 2 shows a transmission/wavelength diagram of a glazing element.

FIG. 2 shows a diagrammatic representation depicting the variance of the transmission setting of the glazing element. The degree of transmission is laid off as ordinate and the wavelength is laid off as abscisse. Curve a indicates the course of the transmission of two uncoated panes 2. Curve b shows the transmission behavior of the glazing element coated in the invented manner in the decolored state, i.e. there is a sufficient amount of oxygen between the panes 2. On the other hand, curve c shows the degree of transmission of the glazing element in the colored state, i.e. the transmission is very low. If the maximum transmission of curve b is approximately 0.75, the minimum value of curve c is only 0.18, i.e. the transmission area which is enclosed by curves b and c can be controlled individually with the aid of a suitable gas flow between the two panes 2.

What is claimed is:

1. A glazing element, in particular, for facing building facades, having two panes enclosing an intermediate space and having a layer structure on at least one pane, surface facing said intermediate space as well as having a gas atmosphere within said intermediate space, characterized by the fact that said layer structure has a reactive layer applied on said one surface of said one pane and a catalytic layer applied on said reactive layer, said catalytic layer activating in said reactive layer, depending on the composition of said gas atmosphere contained between said panes, a reaction which changes the optical and/or electrical properties of said reactive layer, and that means are provided for varying said composition of said gas atmosphere in said intermediate space, thereby making the electrical and/or optical properties of said reactive layer variable.

2. A glazing element according to claim 1, characterized by the fact that said reactive layer contains wolfram oxide, molybdenum oxide, titanium oxide, vanadium oxide, chromium oxide and/or ceric oxide.

3. A glazing element according to claim 2, characterized by the fact that the thickness of the reactive layer ranges between 100 nm and 800 nm.

4. A glazing element according to claim 1 characterized by the fact that said catalytic layer contains platinum, rhodium, palladium and/or nickel.

5. A glazing element according to claim 4, characterized by the fact that the thickness of said catalytic layer ranges between 1 nm and 5 nm.

6. A glazing element according to claim 2 characterized by the fact that the hydrogen portion of the gas atmosphere is raised in order to reduce transmission.

7. A glazing element according to claim 6, characterized by the fact that in an oxygen-free atmosphere, the hydrogen part is approximately 1%.

8. A glazing element according to claim 2 characterized by the fact that the oxygen portion of the gas atmosphere is raised in order to raise transmission.

9. A glazing element according to claim 8, characterized by the fact that in a hydrogen-free atmosphere, the oxygen portion is approximately 0.5%.

10. A glazing element according to claim 8, characterized by the fact that raising transmission occurs by means of atmospheric air.

11. A glazing element according to claim 1, characterized by the fact that a thin layer is provided which is reflecting in the infrared range and is transmissive in the visible range.

12. A glazing element according to claim 11, characterized by the fact that said thin layer is a silver layer or a semiconductor layer.

13. A glazing element according to claim 1 characterized by the fact that said substrate is a glass and/or polymer substrate and/or a metallic substrate.

14. A glazing element according to claim 1, wherein said reaction is effected without input of electrical energy.

15. A glazing element according to claim 1, wherein said composition of said gas atmosphere which is varied is at least one of a concentration of oxygen and a concentration of hydrogen.

16. A glazing element, in particular, for facing building facades, having two panes enclosing an intermediate space and having a layer structure on at least one pane surface facing said intermediate space as well as having a gas atmosphere within said intermediate space, characterized by the fact that said layer structure has a reactive layer applied on said one surface of said one pane and a catalytic layer applied on said reactive layer, said catalytic layer activating in said reactive layer, depending on the composition of said gas atmosphere contained between said panes, a reaction which changes the optical and/or electrical properties of said reactive layer, and that means are provided for varying said composition of said gas atmosphere in said intermediate space, thereby making the electrical and/or optical properties of said reactive layer variable.

17. A glazing element according to claim 16, wherein said reaction is effected without input of electrical energy.

18. A glazing element according to claim 16, wherein said composition of said gas atmosphere which is varied is at least one of a concentration of oxygen and a concentration of hydrogen.

19. A method of controlling the flow of radiation through a multiple paned structure, comprising:

provarding two panes at a distance from one another to define an intermediate space therebetween;

supplying a gas atmosphere to said intermediate space;

applying a reactive layer on a surface of at least one of said panes which faces said intermediate space;

applying a catalytic layer on said reactive layer, said catalytic layer activating said reactive layer depending on a composition of said gas atmosphere to change at least one of optical and electrical properties of said reactive layer; and varying the composition of said gas atmosphere.

20. A method according to claim 19, wherein said catalytic layer activates said reactive layer without input of electrical energy.

21. A method according to claim 19, wherein said composition of said gas atmosphere which is varied is at least one of a concentration of oxygen and a concentration of hydrogen.

22. A multiple pane structure with variable radiation transmissivity, comprising:

two panes arranged at a distance from each other to define an intermediate space therebetween;

a reactive layer disposed on a surface of at least one of said panes, said surface facing said intermediate space;

a catalytic layer disposed on said reactive layer; and a gas to be supplied to said intermediate space, a composition of said gas being variable, said catalytic layer activating said reactive layer in response to the composition of said gas to vary the radiation transmissivity of said reactive layer.

23. A multiple pane structure according to claim 22, wherein said catalytic layer activates said reactive layer without input of electric energy.

24. A multiple pane structure according to claim 22, wherein said composition of said gas which is variable is at least one of a concentration of oxygen and a concentration of hydrogen.

25. A method of varying a radiation transmissivity of a multiple pane structure, comprising:

providing two panes arranged at a distance from each other to define an intermediate space therebetween, a reactive layer being disposed on a surface of at least one of said panes, said surface facing said intermediate space, a catalytic layer being disposed on said reactive layer;

supplying a gas to said intermediate space, a composition of said gas being variable, said catalytic layer activating said reactive layer in response to the composition of said gas to vary the radiation transmissivity of said reactive layer; and varying said composition of said gas.

26. A method according to claim 25, wherein said catalytic layer activates said reactive layer without input of electric energy.

27. A method according to claim 25, wherein said composition of said gas which is variable is at least one of a concentration of oxygen and a concentration of hydrogen.

* * * * *